(12) United States Patent
Pathi et al.

(10) Patent No.: US 8,133,996 B2
(45) Date of Patent: Mar. 13, 2012

(54) PROCESS FOR THE PREPARATION OF ETHYL-N-(2,3-DICHLORO-6-NITROBENZYL)GLYCINE HYDROCHLORIDE

(75) Inventors: Srinivas Laxminarayan Pathi, Karnataka (IN); Rajendra Narayanrao Kankan, Mumbai (IN); Dharmaraj Ramachandra Rao, Maharashtra (IN)

(73) Assignee: CIPLA Limited, Mumbai (IN)

( * ) Notice: Subject to any disclaimer, the term of this patent is extended or adjusted under 35 U.S.C. 154(b) by 156 days.

(21) Appl. No.: 12/525,760

(22) PCT Filed: Feb. 6, 2008

(86) PCT No.: PCT/GB2008/000430
§ 371 (c)(1),
(2), (4) Date: Sep. 17, 2009

(87) PCT Pub. No.: WO2008/096145
PCT Pub. Date: Aug. 14, 2008

(65) Prior Publication Data
US 2010/0075999 A1    Mar. 25, 2010

(30) Foreign Application Priority Data
Feb. 6, 2007  (IN) .......................... 215/MUM/2007

(51) Int. Cl.
*C07D 239/00* (2006.01)
*C07D 487/00* (2006.01)
(52) U.S. Cl. ..................................... 544/250
(58) Field of Classification Search .................. 544/250
See application file for complete search history.

(56) References Cited

U.S. PATENT DOCUMENTS

| | | |
|---|---|---|
| 4,146,718 A | 3/1979 | Jenks et al. |
| 4,208,521 A | 6/1980 | Crenshaw et al. |
| 5,801,245 A | 9/1998 | Lang |
| 6,653,500 B2 | 11/2003 | Lang et al. |

FOREIGN PATENT DOCUMENTS

| | | | |
|---|---|---|---|
| EP | 0 514 917 A1 | * | 11/1992 |
| EP | 0514917 A1 | | 11/1992 |
| WO | WO 02/08228 | * | 1/2002 |
| WO | 2008096145 A1 | | 8/2008 |

OTHER PUBLICATIONS

Foreign communication from the priority application—International Preliminary Report on Patentability, PCT/GB2008/00430, Aug. 11, 2009, 7 pages.

Foreign communication from the priority application—International Search Report and Written Opinion, PCT/GB2008/000430, Jul. 2, 2008, 11 pages.

* cited by examiner

*Primary Examiner* — Noble Jarrell
*Assistant Examiner* — Erich A Leeser
(74) *Attorney, Agent, or Firm* — Conley Rose, P.C.; Rodney B. Carroll

(57) ABSTRACT

The invention relates to a process for the preparation of anagrelide, and for the preparation of intermediates for use in preparing anagrelide. The invention also relates to the intermediates per se, in particular compounds of Formula (V):

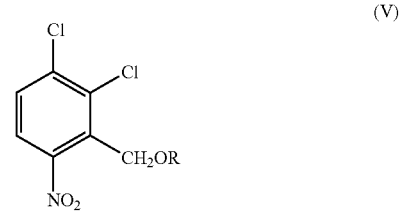

(V)

where R constitutes a suitable leaving group, which may not be hydrogen. The R group may be selected from: (i) —$SiR^1_3$, (ii) —$CH_2Ar$, (iii) —$COOR^2$, and (iv) sulfonates such as —$SO_2R^3$.

12 Claims, No Drawings

PROCESS FOR THE PREPARATION OF ETHYL-N-(2,3-DICHLORO-6-NITROBENZYL)GLYCINE HYDROCHLORIDE

CROSS-REFERENCE TO RELATED APPLICATIONS

This application is a filing under 35 U.S.C. 371 of International Application No. PCT/GB2008/000430 filed Feb. 6, 2008, entitled "Process for the Preparation of Ethyl-N-(2,3-dichloro-6-nitrobenzyl)glycine hydrochloride," claiming priority of Indian Patent Application No. 215/MUM/2007 filed Feb. 6, 2007, which applications are incorporated by reference herein in their entirety.

FIELD OF INVENTION

The present invention relates to an improved process for the preparation of ethyl-N-(2,3-dichloro-6-nitrobenzyl)glycine hydrochloride which is a key intermediate used in the preparation of anagrelide, (6,7-dichloro-1,5-dihydroimidazo[2,1-b]quinazolin-2 (3H)-one.

BACKGROUND OF THE INVENTION

Anagrelide, is a potent reducer of platelet count induced by a variety of aggregating agents and has the following structure

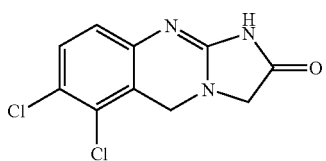

(Formula II)

U.S. Pat. No. 4,146,718 discloses the process for the preparation of ethyl-N-(2,3-dichloro-6-nitrobenzyl)glycine hydrochloride from 1,2,3-trichlorobenzene as depicted in Scheme I via 2,3-dichloro-6-nitrobenzonitrile, which involves the use of poisonous reagents, such as cuprous cyanide. Cyanation is carried out at a temperature of 165° C. which is highly exothermic, uncontrollable and not scalable. 2,3-dichloro-6-nitrobenzonitrile has extreme toxic and skin-irritant properties. Diborane is a flammable gas, used for the reduction of 2,3-dichloro-6-nitrobenzonitrile. The reduction reaction is exothermic, uncontrollable and not feasible industrially.

Scheme I:

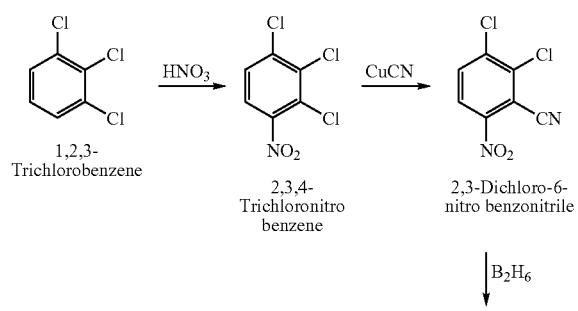

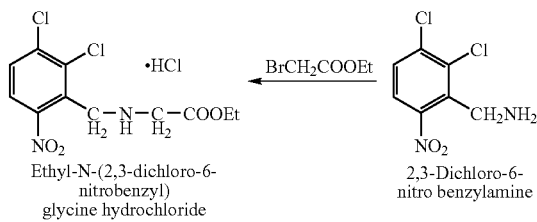

U.S. Pat. No. 5,801,245 discloses process for the preparation of ethyl-N-(2,3-dichloro-6-nitrobenzyl)glycine hydrochloride from 2,3-dichloro toluene as depicted in Scheme II.

Scheme II:

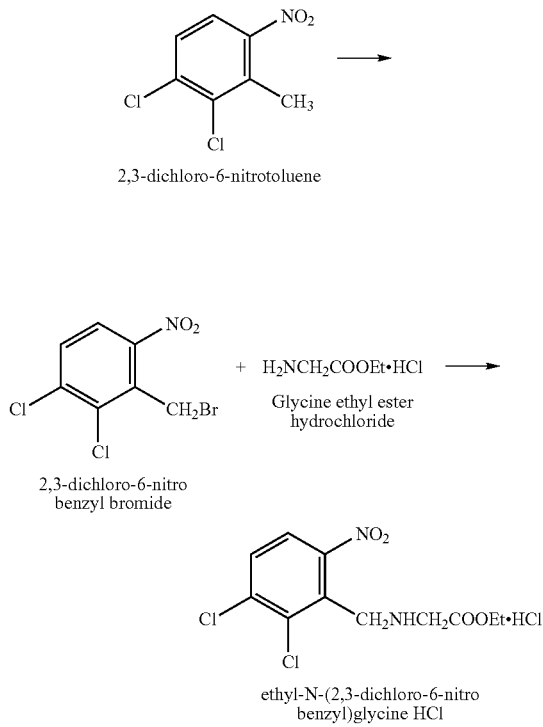

The reaction involves a radical halogenation of the toluene group. The material is purified by column chromatography at each stage which makes the process more tedious and it is not viable industrially. The use of a chromatographic solvent, such as chloroform (which is a known carcinogen), is disadvantageous with respect to industrial application.

US 2003/0060630 discloses a method for making ethyl-N-(2,3-dichloro-6-nitrobenzyl)glycine hydrochloride from 2,3-dichloro benzaldehyde as depicted in Scheme III.

Scheme III:

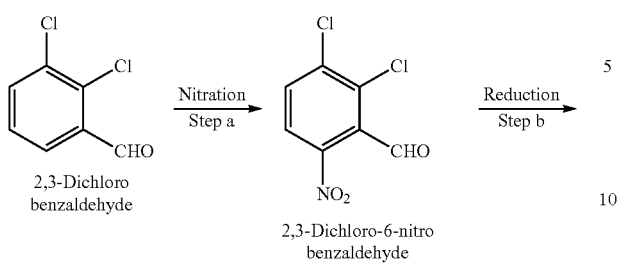

2,3-Dichloro benzaldehyde 2,3-Dichloro-6-nitro benzaldehyde

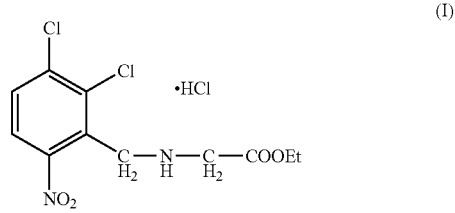

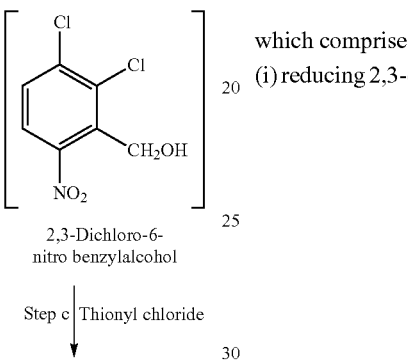

2,3-Dichloro-6-nitro benzylalcohol

Step c | Thionyl chloride

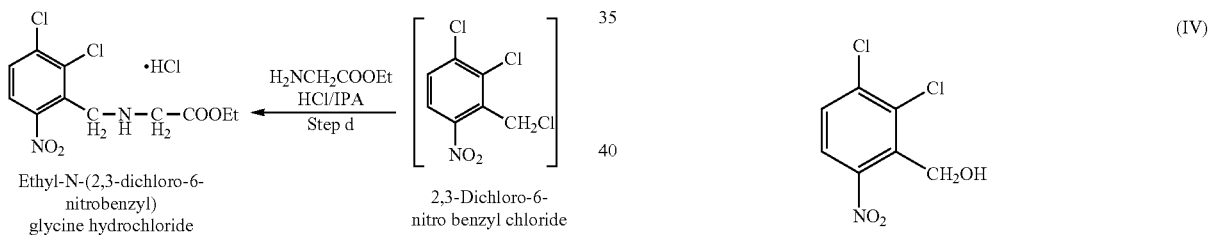

Ethyl-N-(2,3-dichloro-6-nitrobenzyl) glycine hydrochloride 2,3-Dichloro-6-nitro benzyl chloride In step (b), the reduction reaction is carried out in high boiling solvents like toluene. The reduction in step (b) and the chlorination in step (c) are sluggish. Also, the chlorination reaction is exothermic and uncontrollable, which leads to formation of more impurities and thereby resulting in low yield (page 4, column 2, and page 5, column 1: 65%). Hence, this prior art process is not viable for industrial scale up.

Because of the difficulties encountered in the processes disclosed in the prior art, there is a need to develop more efficient and economical synthetic route for the preparation of ethyl-N-(2,3-dichloro-6-nitrobenzyl)glycine hydrochloride, which is suitable for industrial scale up. The present invention relates to a new process for the synthesis of Ethyl-N-(2,3-dichloro-6-nitrobenzyl)glycine hydrochloride.

An object of the present invention is to provide a novel process for the synthesis of the intermediate ethyl N-(2,3-dichloro-6-nitrobenzyl)glycine hydrochloride.

Another object of the present invention is to provide novel process for synthesis of anagrelide.

Yet, another object of the present invention is to provide a simple novel process which is useful for application on an industrial scale.

SUMMARY OF THE INVENTION

The present invention provides a new process for the synthesis of ethyl-N-(2,3-dichloro-6-nitrobenzyl)glycine hydrochloride, a compound of Formula (I)

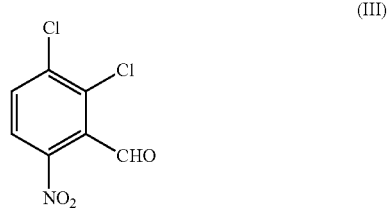

which comprises the following steps;
(i) reducing 2,3-dichloro-6-nitro benzaldehyde Formula (III), (III)

[structure]

to form 2,3-dichloro-6-nitro benzyl alcohol of Formula (IV), (IV)

[structure]

(ii) reacting 2,3-dichloro-6-nitro benzyl alcohol with suitable compound to obtain compound of Formula (V),

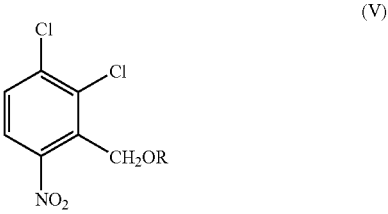

where R constitutes a suitable leaving group, which may not be hydrogen.

Preferably, the group R is selected from:

i) —SiR$^1{}_3$, where R$^1$ is a substituted or unsubstituted alkyl. R$^1$ is preferably C$_1$ to C$_6$, more preferably C$_1$ to C$_4$ straight or branched chain alkyl group. Most preferably R$^1$ is methyl.

ii) —CH$_2$Ar, where Ar stands for aryl, preferably a substituted or unsubstituted phenyl group.

iii) —COOR², where R² is alkyl or aryl. When R² is alkyl it is preferably C₁ to C₆, more preferably C₁ to C₄ straight or branched chain alkyl. When R² is alkyl, it is most preferably methyl. The aryl group is preferably a substituted or unsubstituted phenyl group.

iv) sulfonates such as —SO₂R³, where R³ is alkyl or aryl. When R³ is alkyl it is preferably C₁ to C₆, more preferably C₁ to C₄ straight or branched chain alkyl. When R³ is alkyl, it is most preferably methyl. The aryl group is preferably a substituted or unsubstituted phenyl group.

The most preferred —O—R groups in Formula (V) are mesylate, besylate and tosylate.

(iii) Alkylating the compound of Formula (V) with glycine ethyl ester in a suitable solvent, using a base, and then converting to a salt, preferably the hydrochloride salt, in a suitable solvent, to obtain compound of Formula (I).

It will be appreciated that step (i) is optional, in that the compound of Formula (IV) may be provided by any suitable means.

Thus, according to one aspect of the invention there is provided a process for the synthesis of a compound of Formula (V)

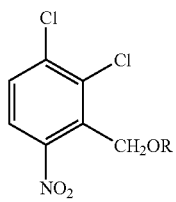
(V)

where R is a suitable leaving group, which may not be hydrogen, said process comprising reacting a compound of Formula (IV)

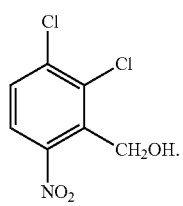
(IV)

with suitable compound to obtain the compound of Formula (V).

Preferably, the reaction is carried out in the presence of an alkyl or aryl sulphonyl halide, especially a methyl sulphonyl halide, such as methyl sulphonyl chloride. Preferably also, the reaction is carried out in the presence of a base, such as triethylamine. Preferably, the reaction is carried out at a temperature of 35° C., or less.

According to another aspect of the invention there is provided a process for preparing a compound of Formula (I'),

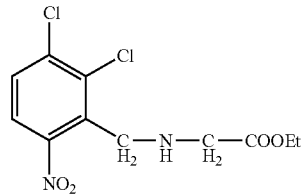
(I')

said processing comprising alkylating a compound of Formula (V)

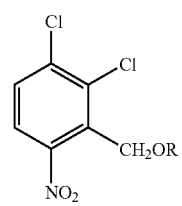
(V)

where R constitutes a suitable leaving group, which may not be hydrogen (preferably as described above) with glycine ethyl ester in a suitable solvent, using a base.

The compound of Formula (I') may be converted to a salt in the presence of a suitable solvent. Most preferably, the compound of Formula (I') is converted to the hydrochloride salt in a suitable solvent, to obtain compound of Formula (I).

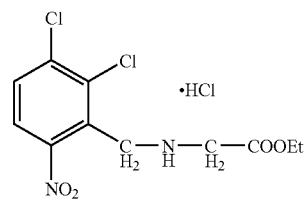
(I)

The reaction temperature of the alkylation step is preferably 60° C., or lower, more preferably 40° C., or lower.

According to another aspect of the invention there is provided a compound of Formula (V):

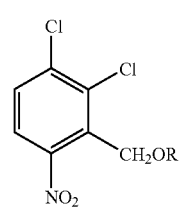
(V)

where R is a suitable leaving group, which may not be hydrogen, and is preferably as described above.

In another aspect, the present invention provides a process to prepare anagrelide of Formula (II) which comprises the following steps:

(i) Forming a salt of the compound of Formula (I') (the hydrochloride salt is preferred, Formula (I) using the process described above;

(ii) reducing the nitro group of Formula (I) with a suitable reducing agent to convert it to an amine of Formula (VI),

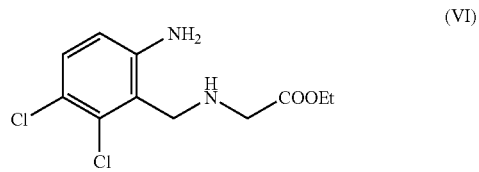

(VI)

(iii) reacting the compound of Formula (VI) with a cyanogen halide to form compound of Formula (VII),

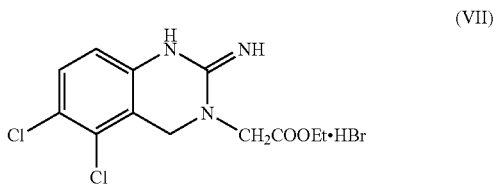

(VII)

wherein halide is chloro, bromo or iodo;

(iv) cyclising compound of Formula (VII), to form compound of Formula (II), i.e. anagrelide.

The anagrelide formed by the processes described above may be combined with a suitable carrier to make a pharmaceutical composition. Such compositions may be used to reduce platelet count induced by a variety of aggregating agents.

DETAILED DESCRIPTION OF THE INVENTION

The process according to the invention will now be described in more detail below.

The process for the preparation of ethyl-N-(2,3-dichloro-6-nitrobenzyl)glycine hydrochloride according to the invention is depicted in the reaction scheme below. Brackets indicate intermediates that could be isolated but are not usually isolated in the integrated process.

Scheme IV:

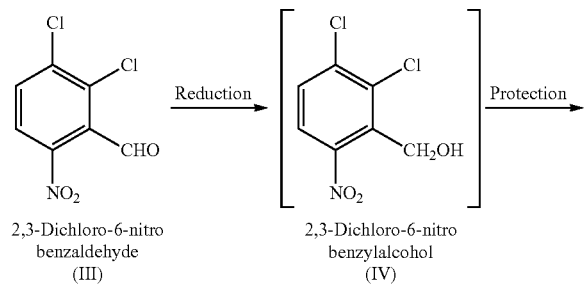

2,3-Dichloro-6-nitro benzaldehyde (III) → Reduction → 2,3-Dichloro-6-nitro benzylalcohol (IV) → Protection →

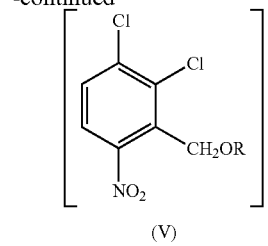

(V)

Acetonitrile
H$_2$NCH$_2$COOEt
HCl(g) in IPA/Ethyl acetate

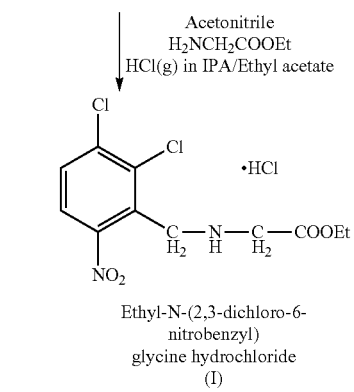

Ethyl-N-(2,3-dichloro-6-nitrobenzyl) glycine hydrochloride (I)

wherein R represents a suitable leaving group, wherein R is not hydrogen and preferably has the meaning described above in relation to Formula (V).

(i) 2,3-dichloro-6-nitrobenzaldehyde, of Formula (III) is reduced to give the corresponding alcohol of Formula IV. The reducing agent is preferably selected from sodium borohydride, potassium borohydride, sodium cyanoborohydride and tetramethyl ammonium borohydride. The reaction is preferably carried out in a solvent, which is preferably a $C_1$ to $C_6$ straight chain or branched chain alcohol, especially methanol, ethanol, isopropanol or n-butanol; or a chlorinated solvent such as chloroform, methylene chloride, carbon tetrachloride, ethylene chloride, with methylene chloride being preferred. The reaction is preferably carried out at a temperature ranging from 0° C. to the reflux temperature of the solvent, and the reaction time may vary from 1 to 3 hrs.

(ii) According to a particular feature of the present invention, the hydroxymethyl functionality of phenyl methyl alcohol of Formula (IV) is protected with suitable protecting group R (as discussed above in relation to Formula (IV) using variety of methods.

Various organic or inorganic bases may be employed, such as triethylamine, pyridine or potassium carbonate, with triethylamine being preferred.

For example, one method includes reacting 2,3-dichloro-6-nitro benzyl alcohol—Formula (IV)—with alkyl or aryl sulphonyl halide in the presence of a base, such as triethylamine or the like, preferably at a temperature of 35° C., or less, for a time preferably less than 8 hours. The sulphonyl halide is preferably added to the compound of Formula (IV) over an extended period of time at a temperature of 30° C., or less, with stirring. The reaction is not exothermic, which avoids impurity formation. The organic layer may then be separated, washed with an acid and neutralized with a base, then concentrated to obtain the compound of Formula (V).

The alkyl sulphonyl halide is preferably $C_1$ to $C_6$, more preferably $C_1$ to $C_4$ straight or branched chain alkyl. The alkyl sulphonyl halide is most preferably methyl sulphonyl halide. In the aryl sulphonyl halide, the preferred aryl groups are phenyl and p-toluyl.

Steps (i) and (ii) are preferably carried out without isolating the alcohol of Formula (IV).

(iii) According to yet another embodiment of the present invention the compound of Formula (V) is alkylated with glycineethylester in an organic solvent, such as acetonitrile, using base and a catalyst preferably, dimethyl amino pyridine. Suitable bases for this reaction are carbonates or alkali metal hydroxides, preferably anhydrous potassium carbonate. Typically, the reaction is carried out at a temperature less than or equal to 60° C., more preferably less than or equal to 40° C. After completion of the reaction, the reaction mass is filtered, and concentrated under vacuum to obtain ethyl-N-(2,3-dichloro-6-nitrobenzyl)glycine, which is further converted to hydrochloride salt in suitable organic solvent such as ethyl acetate to obtain ethyl-N-(2,3-dichloro-6-nitrobenzyl)glycine hydrochloride, a compound of Formula (I).

In prior art processes, where the leaving group is bromo (e.g. U.S. Pat. No. 5,801,245, column 5, example 3, lines 6-25), the reaction with glycine ethyl ester hydrochloride requires 14 hrs reflux in THF-triethylamine, which requires further purification by column chromatography. Yield—87% w/w—Efficiency 60.20%.

In prior art processes, when the leaving group is chloro (e.g. US 2003/0060630, page 5 [0040]), the reaction is carried out in high boiling solvent toluene, at 80° C. for 24 hrs using 10% w/w cetyltrimethylammonium bromide, which is an expensive catalyst—Efficiency 66-71%.

In the process according to the invention, where the leaving group is mesyl or tosyl, for example, the reaction can be carried out at low temperature of 37-40° C. in acetonitrile as solvent, potassium carbonate as base and 0.2% w/w dimethyl amino pyridine as catalyst. Due to the low reaction temperature, a relatively small level of impurities is formed giving high yield and purity—Efficiency 75.52%.

In another aspect of the present invention, intermediate ethyl-N-(2,3-dichloro-6-nitrobenzyl)glycine hydrochloride of Formula (I), prepared by using process of the present invention, is converted to anagrelide by (iv) Reducing nitro group of Formula (I) with suitable reducing agent to convert it to amine of Formula (VI). Various methods may be employed to carry out the nitro reduction, such as catalytic hydrogenation or metal reduction. Normally catalytic hydrogenation is carried out in the presence of noble metal catalysts, such as palladium, platinum, or Raney Nickel on a carbon support. The source of hydrogen may be hydrogen gas or a hydrogen donating compound such as ammonium formate. Metal reduction may be carried out using tin, iron, or using stannous chloride with an acid.

In the forgoing processes the preferred reduction is metal reduction using stannous chloride and a preferred acid is hydrochloric acid. The reaction is preferably carried out at a temperature of 50° C., or less. After completion of the reaction, the reaction mass is filtered, suspended in water and basified to obtain an amine of Formula (VI).

(v) Reacting the compound of Formula (VI) with cyanogen halide to form the compound of Formula (VII) where the halide is as defined above, i.e., chloro, bromo or iodo. Normally the reaction is carried out using cyanogen bromide in an aprotic inert organic solvent such as toluene, chlorobenzene, xylene, heptane and hexane. A preferred solvent is toluene. A preferred reaction temperature is from 80-150° C.

(vi) Cyclising compound of Formula (VII), to form a compound of Formula (II), i.e. anagrelide. The compound, ethyl-N-(5,6-dichloro-3,4-dihydro-2(1H) iminoquinazoline-3-acetate hydrobromide of Formula (VII), is readily converted to anagrelide of Formula (II) with an organic base, such as triethylamine or dimethylaniline. The reaction may be carried out in an inert solvent.

The intermediate compound of Formula (V) represents a novel compound, per se, and this novel intermediate forms further aspects of the present invention.

In the present invention, the reaction is carried out by protecting the hydroxymethyl functionality of compound of Formula (IV). When using methane sulphonyl chloride in methylene chloride, the reaction was less exothermic than in the prior art, and was more controllable with less impurity formation.

Overall yield:—76% (From compound III to compound I) with HPLC purity of 98.5%

EXAMPLES

Further details of the invention are given in the examples below. The examples are provided for illustration only.

Example 1

Preparation of 2,3-dichloro-6-nitro benzyl methane sulphonate, a Compound of Formula (V)

Methylene chloride (2000 ml) and sodium borohydride (120 g) were charged to a clean and dry flask and chilled to 0-5° C. Methanol (100 ml) was added slowly over a period of 20 minutes followed by 2,3-dichloro-6-nitro benzaldehyde solution (500 g in 2000 ml of methylene chloride) over a period of 2 hours maintaining the temperature at 0-5° C. and the contents were stirred at 0-5° C. for 1 hour. After completion of reaction, water (3000 ml) was added and stirred for 10 minutes. The organic layer was separated, dried over sodium sulphate and was filtered to get a clear filtrate.

To the clear filtrate triethylamine (460 ml), was slowly added over a period of 1 hour at 10-15° C., then methane sulphonyl chloride (325 ml) was added drop wise over a period of 2 hours maintaining temperature of 10-15° C. and the reaction mass was allowed to attain room temperature. Further the reaction mass was stirred at room temperature for 5 hours and after completion of reaction, the organic layer was washed with water (1000 ml) twice, followed by 1N HCl solution (1000 ml) twice, 5% Sodium bicarbonate solution (1000 ml) twice, water (1000 ml) twice and was dried over sodium sulfate. The clear organic layer was concentrated under vacuum below 40° C. to give the title compound which was used in the next step.

Example 2

Preparation of ethyl-N-(2,3-dichloro-6-nitrobenzyl)glycine hydrochloride, a Compound of Formula (I)

2,3-dichloro-6-nitro benzyl methane sulphonate (Example 1) was dissolved in acetonitrile (2400 ml). To this reaction mass were charged anhydrous Potassium carbonate (480 g), dimethyl amino pyridine (480 mg) and glycine ethyl ester (240 g) at room temperature. The contents were stirred at 37-40° C. for 24 hours. After completion of reaction, the insolubles were filtered, washed with acetonitrile (120 ml). The clear filtrate was concentrated and stripped off using ethyl acetate (240 ml).

Further ethyl acetate (1200 ml) was added, chilled the contents to 5-10° C., adjusted the pH to 2.0 using IPA-HCl at 5-10° C. The contents were stirred at 5-10° C. for 1 hour. The solids were filtered, washed with chilled ethyl acetate (120 ml) and dried under vacuum at room temperature for 4 hours to give the title compound (595 g, 76% yield, 98.5% HPLC purity).

Example 3

Preparation of Anagrelide, a Compound of Formula (II)

a) Preparation of Ethyl-5,6-dichloro-3,4-dihydro-2[1H]-imino quinazolin-3-acetate hydrobromide A solution of stannous chloride dihydrate (1850 gms) in concentrated HCl (6.7 liters) was added slowly to a cooled solution of ethyl-N-(2,3-dichloro-6-nitrobenzyl)glycine hydrochloride (595 gms) in concentrated HCl (5.15 liters) maintaining temperature 15-20° C. over a period of 2 hours. The contents were heated slowly to 40-45° C. and stirred for 1 hour at 40-45° C. After completion of reaction, the contents were cooled to 15-20° C., maintained for 15 minutes and filtered.

The solids thus obtained were suspended in water (2.9 liters), adjusted the pH of the reaction mass to 8.0-9.0 using potassium carbonate solution (prepared by dissolving 376 gms of potassium carbonate in 4.25 liters of water) at 0-5° C., extracted into toluene (3.0 liters×3), dried over sodium sulphate and clarified.

To the clear toluene layer, added Cyanogen bromide solution (prepared by dissolving 222 gms of cyanogen bromide in 655 ml of toluene) in 30 minutes maintaining temperature 15-20° C. and stirred at 25-30° C. for 2 hours. The contents were heated slowly to 105-110° C. maintained for 16 hours at 105-110° C. After completion of reaction, the mass was cooled to 15-20° C. and stirred for 45 minutes. Filtered the material, washed with chilled toluene (1.3 liters). The material was slurried in toluene (470 ml) at 15-20° C. for 1 hour, filtered, washed with cold toluene (160 ml) and dried under vacuum at 50-60° C. for 8 hours to give the title compound (445 gms).

b) Preparation of 6,7-Dichloro-1,5-dihydroimidazo[2,1-b]quinazolin-2(3H)-one [Anagrelide]

A mixture of ethyl-5,6-dichloro-3,4-dihydro-2(1H)-iminoquinazolin-3-acetate hydrobromide (445 gms), isopropyl alcohol (4.45 liters) and triethylamine (246 ml) was refluxed for 2 hours. After completion of reaction, the mixture was cooled to 20-25° C., filtered, washed with chilled isopropyl alcohol (1.0 liters) and dried under vacuum at 50-55° C. for 6 hours to give the title compound (285 gms).

It will be appreciated that the invention described above may be modified within the scope of the claims.

What is claimed is:

1. A process for preparing anagrelide of Formula (II):

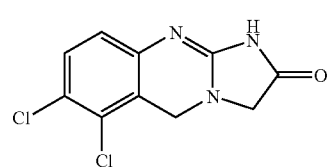

which comprises:

(i) alkylating a compound of Formula (V):

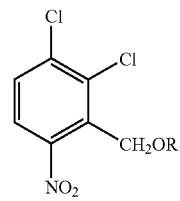

where R is a leaving group other than hydrogen with glycine ethyl ester in a suitable solvent, using a base, to produce a compound of Formula (I'):

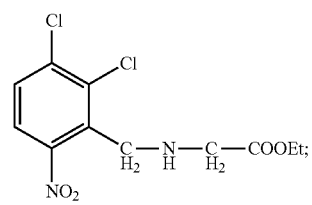

(ii) converting the compound of Formula (I') to the hydrochloride salt in a suitable solvent, to obtain compound of Formula (I):

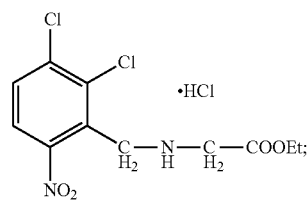

(iii) reducing the nitro group of Formula (I) with a suitable reducing agent to convert it to an amine of Formula (VI):

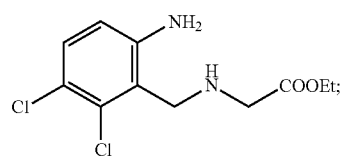

(iv) reacting the compound of Formula (VI) with a cyanogen halide to form compound of Formula (VII):

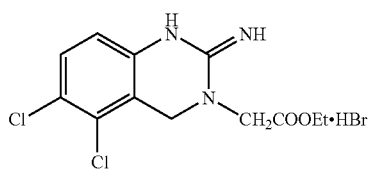

wherein halide is chloro, bromo or iodo; and (v) cyclising compound of Formula (VII), to form compound of Formula (II).

2. The process according to claim 1, wherein the group R is —SiR$^1_3$, where R$^1$ is a substituted or unsubstituted alkyl.

3. The process according to claim 1, wherein the group R is —CH$_2$Ar, where Ar stands for aryl.

4. The process according to claim 1, wherein the group R is —COOR$^2$, where R$^2$ is alkyl or aryl.

5. The process according to claim 1, wherein the group R is —SO$_2$R$^3$, where R$^3$ is alkyl or aryl.

6. The process according to claim 1, wherein a compound of Formula (IV):

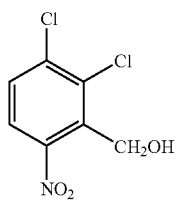

(IV)

is reacted to produce a compound of Formula (V):

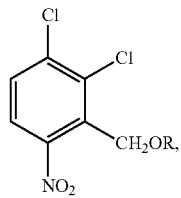

(V)

where R is a leaving group other than hydrogen.

7. The process according to claim 6, wherein the reaction is carried out in the presence of an alkyl or aryl sulphonyl halide.

8. The process according to claim 6, wherein the reaction is carried out in the presence of a base.

9. The process according to claim 6, wherein the reaction is carried out at a temperature of 35° C., or less.

10. The process according to claim 6, wherein a compound of Formula (III)

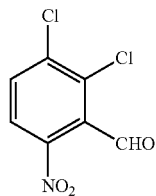

(III)

is reduced to form the compound of Formula (IV):

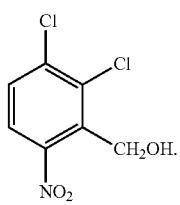

(IV)

11. The process according to claim 10, wherein the compound of Formula (IV) is not isolated.

12. The process according to claim 1, wherein the reaction temperature of the alkylation step is 60° C., or lower.

* * * * *